United States Patent [19]

Adamus et al.

[11] Patent Number: 5,474,934
[45] Date of Patent: Dec. 12, 1995

[54] BIODEGRADATION OF ETHERS

[75] Inventors: Jean E. Adamus, North Plainfield; Harold D. May, Highbridge, both of N.J.; Domenic A. Paone, Easton, Pa.; Patrick J. Evans, Highland Park; Rebecca E. Parales, Bound Brook, both of N.J.

[73] Assignee: Celgene Corporation, Warren, N.J.

[21] Appl. No.: 181,998

[22] Filed: Jan. 13, 1994

[51] Int. Cl.$^6$ .............................. C02F 3/02; C12N 1/20; C12S 13/00

[52] U.S. Cl. ................ 435/262.5; 435/262; 435/252.1; 210/620

[58] Field of Search .............................. 435/262, 262.5, 435/252.1, 252.32, 253.1; 210/620

[56] References Cited

U.S. PATENT DOCUMENTS 4,643,899  2/1987  Kerr et al. ................................. 426/2

FOREIGN PATENT DOCUMENTS 1375646  2/1988  U.S.S.R. .

OTHER PUBLICATIONS

Adams et al., "Combined Treatment Technologies: Effects Of Advanced Oxidation Pretreatment On Biodegradability of 1,4–Dioxane And 2–Methyl–1,3–dioxolane", I&EC Special Symposium, American Chemical Society, Atlanta, Georgia, pp. 485–488 (Sep. 27–29, 1993).
Battersby et al., "Survey of the Anaerobic Biodegradation Potential of Organic Chemicals in Digesting Sludge", *Applied and Environmental Microbiol.*, 55:2, pp. 433–439 (1989).
Bernhardt et al., "Degradation of dioxane, tetrahydrofuran and other cyclic ethers by an environmental Rhodococcus strain", *Appl. Microbiol. Biotechnol.*, 36, pp. 120–123 (1991).
Brown et al., "The effect of withdrawal of morpholine from the influent and its reinstatement on the performance and microbial ecology of a model activated sludge plant treating a morpholine–containing influent", *J. Appl. Bacteriol.*, 69, pp. 43–53 (1990).
Brown et al., "Instability of the morpholine–degradative phenotype in mycobacteria isolated from activated sludge", *J. Appl. Bacteriol.*, 69, pp. 54–62 (1990).
Burback et al., "Biodegradation and Biotransformation of Groundwater Pollutant Mixtures by Mycobacterium vaccae", *Applied and Environmental Microbiol.*, 59:4, pp. 1025–1029 (Apr. 1993).
Calamari et al., "Biodegradation and Toxicity of Selected Amines on Aquatic Organisms", *Chemosphere*, 9, pp. 753–762 (1980).
Cech et al., "Isolation and Identification of a Morpholine–Degrading Bacterium", *Appl. and Env. Microbiol.*, 54:2, pp. 619–621 (Feb. 1988).
Cech et al., "Biological Destruction of Morpholine", *Khimiya i Tekhnologia Vody*, 9:5, pp. 90–93 (1987).
Chudoba et al., "Determination of Kinetic Constants of Activated Sludge Microorganisms Responsible for Degradation of Xenobiotics", *Wat. Res.*, 23:11, pp. 1431–1438 (1989).
Dmitrenko et al., "Selection of Destructor Microorganisms for Heterocyclic Xenobiotics", *Khimiya i Tekhnologia Vody*, 9:5, pp. 77–81.
Flathman et al., "Remediation of Contaminated Ground Water Using Biological Techniques", *Ground Water Monitoring*, 9, pp. 105–119 (1989).
Knapp et al., "Morpholine Biodegradation", *International Biodeterioration*, 24, pp. 299–306 (1988).
Knapp et al., "The microbial degradation of morpholine", *J. Appl. Bacteriol.*, 52, pp. 5–13 (1982).
Knapp et al., "The Biodegradation of Morpholine in River Water and Activated Sludge", *Environmental Pollution*, 68, pp. 67–79 (1990).
Matsui et al., "Experience Of 16 Years' Operation And Maintenance Of The Fukashiba Industrial Wastewater Treatment Plant Of The Kashima Petrochemical Complex—II. Biodegradability Of 37 Organic Substances And 28 Process Wastewaters", *Wat. Sci. Technol.*, 20:10, pp. 201–210 (1988).
Orlowska et al., "Characteristics Of Activated Sludge Adapted To Dioxane And N–methylpyrrolidine", *Environment Protection Engineering*, 10:1, pp. 47–57 (1984).
Strotmann et al., "Degradation Of Morpholine In Several Biodegradation Tests And In Wastewater Treatment Plants", *Chemosphere*, 26:9, pp. 1729–1742 (1993).
Subrahmanyam et al., "Wastewater Treatment Of A Phthalate Plasticizer, Ethanolamine And Morpholine Manufacturing Plant: A Case Study", Proceedings 37th Industrial Waste Conference, West Lafayette, Indiana, May 11–13, 1982, pp. 13–20 (1983).
Swain et al., " Biochemical studies of morpholine catabolism by an environmental mycobacterium", *Appl. Microbiol. Biotechnol.*, 35, pp. 110–114 (1991).
Tessier et al., "Degradation of Polyoxyethylenes: Biodegradation Using an Enzyme from Pseudomonas P 400 and Chemical Degradation Using Sodium Hypochlorite", *J. Chem. Research (S)*, pp. 174–175 (1983).
Tölgyessy et al., "The Effect Of Gamma Radiation On Biodegradability Of Morpholine In Aqueous Solution", *J. Radioanal. Nucl. Chem., Letters*, 107:5, pp. 291–295 (1986).
Walton et al., "Physicochemical Properties As Predictors Of Organic Chemical Effects On Soil Microbial Respiration", *Environmental Toxicology and Chemistry*, 8, pp. 53–63 (1989).
Waterhouse et al., "Physical characterisation of plasmids in a morpholine–degrading mycobacterium", *FEMS Microbiol. Lett.*, 80, pp. 305–310 (1991).

Primary Examiner—William H. Beisner
Assistant Examiner—T. J. Reardon
Attorney, Agent, or Firm—Mathews, Woodbridge & Collins

[57] ABSTRACT

Ethers including dioxanes are degraded by bringing an ether-containing influent into intimate contact, under growth or resting conditions and in the presence of oxygen, with a culture comprising a bacterium having the characterizing microbiological properties of Amycolata ATCC 55486 or a mutant thereof which retains the characterizing microbiological property of being capable of utilizing dioxane as a sole carbon growth source.

10 Claims, No Drawings

BIODEGRADATION OF ETHERS

The present invention pertains to the biodegradation of ethers.

In particular it relates to a process for the degradation of ethers, including cyclic ethers of the dioxane type, in which the ether is brought into intimate contact, under growth or resting conditions and in the presence of oxygen, with a bacterial strain capable of utilizing dioxane as a carbon growth source.

BACKGROUND OF THE INVENTION

Various cyclic ethers such as tetrahydrofuran, tetrahydropyran, 1,4-dioxane, 1,3-dioxane, 2-methyl-1,3-dioxolane, etc. which are generated as chemical by-products or have been used as industrial solvents, are recognized as constituting environmental problems, particularly because of their toxicity and/or carcinogenicity.

Chemical methods of degrading dioxane using hydrogen peroxide and ozone in the presence of ultraviolet radiation currently are in operation but suffer from high cost.

While biodegradation has been reported for tetrahydrofuran, diethers having the cyclic dioxane type of structure have proven to be remarkably refractory to biological degradation and generally are considered not to be readily biodegradable. Degradation of dioxane has occasionally been reported but only in the presence of a cometabolite. No bacterial microorganism appears to be known which can use dioxane as its sole carbon source for growth.

Battersby et al., *Appl. Environ. Microbiol.*, 55, 433–439 (1989) reported on the anaerobic biodegradation of 77 organic compounds and found little degradation potential for furan and tetrahydrofuran.

In an examination of 37 pollutants in industrial wastewater of a petrochemical plant utilizing activated sludge, Matsui et al., *Wat. Sci. Tech.*, 20, No. 10, 201–210 (1988), found 4,4-dimethyl-1,3-dioxane was not biodegradable.

Burback et al., *Appl. Environ. Microbiol.*, 59, 1025–1029 (1993) report that less than 50% of dioxane was degraded by Mycobacterium vaccae. Dioxane did not support the growth of this organism.

Because of the biorefractory behavior of 1,4-dioxane and 2-methyl-1,3-dioxolane, Adams et al., American Chemical Society Preprint Extended Abstract, I&EC Special Symposium, Atlanta GA, 485–488 (1993) employed a chemical oxidative pretreatment to enhance biodegradability.

Of six strains of Rhodococcus identified by Bernhardt et al., *Appl. Microbio. Biotechnol.*, 36, 120–123 (1991) as having the ability to degrade tetrahydrofuran, only two were found to degrade dioxane. Despite considerable efforts, no strain was isolated or enriched when dioxane (or cyclohexane) was used as the carbon source.

DETAILED DESCRIPTION

The present invention pertains to a method for biodegrading aliphatic and cyclic ethers and to a biologically pure culture which can use dioxane as the sole source of carbon for bacterial growth.

A bacterial microorganism, actinomycete, genius Aamycolata has been isolated and deposited under the Budapest ockville, Md., 20852, as ATCC 55486. While this microorganism has the ability, shared with several known organisms, of degrading aliphatic ethers such as diethyl ether and methoxybutane and some simple cyclic ethers such as tetrahydrofuran, it has as a characteristic property the ability to utilize 1,4-dioxane and 1,3-dioxane or dioxanes as its sole carbon source for growth and energy. The following description concentrates on the dioxanes because, of cyclic ethers, they appear to be the most refractory to biological degradation. As will be seen, however, the organism also can be utilized to degrade other aliphatic and cycloaliphatic ethers.

Growth of this organism with degradation of 1,4-dioxane occurs at concentrations of as high as 10,000 ppm 1,4-dioxane and at temperatures of from about 10° to about 42° C., typically from about 15° to about 35° C. It has the ability to reduce 1,4-dioxane levels to <10 ppb. The optimal pH for growth and 1,4-dioxane degradation appears to lie within the range of from about 5 to about 8. The culture can be stored for at least 1 month at 4° C. with little loss of activity. Activity is maintained indefinitely at −70° C. as long as the cultures are stored in basal salts medium. The addition of cryoprotectants such as skim milk or glycerol to the storage medium does not appear to be necessary.

Isolation of the organism is achieved through a multi-step process which initially involves aerobic incubation of a 1,4-dioxane-containing material (as for example industrial sludge) in the presence of 100–300 ppm of tetrahydrofuran in a basal salts medium (BSM) containing 0.1% w/v yeast extract. Once degradation of tetrahydrofuran is established, the culture is supplied with both tetrahydrofuran and 100–500 ppm of 1,4-dioxane. Transfer cultures degrade tetrahydrofuran and dioxane to <1 ppm within 78 hours.

Cultures from the initial enrichment are combined and placed in an aerated fermenter containing BSM and 0.1% w/v yeast extract. This culture is supplied with tetrahydrofuran and 1,4-dioxane. After the tetrahydrofuran is depleted (<1 ppm), only 1,4-dioxane is supplied and degradation is allowed to continue without addition of tetrahydrofuran. A typical pattern of dioxane degradation following this protocol is as follows:

| Development of 1,4-dioxane degradation | | |
|---|---|---|
| | Concentration (ppm) | |
| Time (Days) | tetrahydrofuran | 1,4-Dioxane |
| 0 | 139 | 571 |
| 1 | 31 | 517 |
| 2 | <1 | 413 |
| 5 | — | 17 |
| 5  1,4-dioxane added | — | 447 |
| 6 | — | 335 |
| 7 | — | 209 |
| 8 | — | 90 |
| 8  1,4-dioxane added | — | 222 |
| 9 | — | 125 |
| 9  1,4-dioxane added | — | 467 |
| 11 | — | 173 |
| 12 | — | 94 |

Eventually 1000 ppm of 1,4-dioxane can be supplied to the culture daily. This culture, given the designation "CB1184", represents a mixed population which includes irregularly branched, filamentous organisms with clumps or mats of organisms formed within these filaments. The specific rate of 1,4-dioxane degradation is about 0.2–0.3 μg/min-mg protein at 300 ppm 1,4-dioxane (2–3 nmol/min-mg protein).

While this culture contains eucaryotic (protozoa, fun-gal-like and yeast-like microorganisms) and procaryotic (bacterial) organisms, the degradation of dioxane is traceable to the procaryotic organisms. Treatment with 50 µg/mL of procaryotic antibiotics such as tetracycline, streptomycin, and penicillin thus inhibits the degradation of 1,4-dioxane; treatment with an inhibitor of eucaryotic protein synthesis, cycloheximide, does not inhibit the degradation of 1,4-dioxane as can be seen from the following:

| Time (Hrs) | 1,4 Dioxane Concentration (ppm) with the following amendments | | | | |
|---|---|---|---|---|---|
| | None | Cyclo-heximide | Peni-cillin | Streptomycin | Tetracycline |
| 0 | 542 | 541 | 569 | 551 | 492 |
| 24 | 458 | 447 | 543 | 558 | 532 |
| 73 | 391 | 298 | 465 | 519 | 550 |
| 99 | 283 | 160 | 377 | 547 | 470 |
| 121 | 111 | <1 | 328 | 541 | 520 |

Continued transfer and enrichment of the initial culture in the presence of 100 ppm cycloheximide, high levels of 1,4-dioxane (5000–10,000 ppm), and no yeast extract result in isolation of a semipurified consortium containing a filamentous, irregularly branched organism. This consortium was given the designation "CB1185".

The pure culture corresponding to ATCC 55486 can be obtained from this consortium in the following way.

First, the culture designated CB1185 is streaked onto ammonium mineral salts medium (AMS) plates containing 2000 ppm 1,4-dioxane and cultured to produce rough and irregular colonies, dry and white on the top and pale orange underneath. Microscopic observation (1000×) should indicate the presence of irregularly branching filamentous organisms as well as several types of bacterial rods.

An isolated colony then can be streaked onto an AMS plate containing 2000 ppm 1,4-dioxane and incubated at 30° C. for two weeks. This process is repeated until observation of an isolated white colony at 1000× magnification shows a pure culture of stationary, irregularly branching thick rods and filaments, with no small rods present. Colonies appear dry and white on top, and cream to orange underneath. Note should be taken that this organism appears to grow on AMS plates without addition of a carbon source, presumably through use of agar (or agar contaminants) or cellular storage materials as its carbon source. A biologically pure culture obtained in this manner was designated CB1190, and deposited as ATCC 55486.

A single colony obtained in this fashion was inoculated into 50 mL of 1×AMS containing 331 ppm of 1,4-dioxane. This preparation was incubated on a shaker at room temperature and 1,4-dioxane concentration monitored periodically by gas chromatography (GC). The results are as follows:

| Day | Time | 1,4 Dioxane (ppm) | |
|---|---|---|---|
| | | CB1190 | Abiotic Control |
| 0 | 16:30 | 331 | |
| 14 | 9:30 | 345 | |
| 19 | 9:30 | 294 | |
| 31 | 9:30 | 69 | |
| 31 | 1,4 (dioxane added) | 414 | 485 |
| 32 | 9:30 | 310 | 480 |
| 32 | 16:30 | 232 | 468 |
| 33 | 9:30 | 72 | 442 |

-continued

| Day | Time | 1,4 Dioxane (ppm) | |
|---|---|---|---|
| | | CB1190 | Abiotic Control |
| 33 | 13:30 | 28 | n.d.* |
| 34 | 13:30 | <50 ppb | 477 |

*n.d. = not determined

Purity of the culture is monitored by microscopic observation (1000×), and by periodic plating on AMS plus 2000 ppm 1,4-dioxane and Difco Luria agar plates. A single colony type should grow on the 1,4-dioxane plates. Little or no growth occurs on Luria agar if the culture is pure.

The doubling time in AMS medium with approximately 500 ppm 1,4-dioxane at 30° C. is approximately 30 hours. When measured by the increase in optical density, growth of the microorganism correlates inversely with the measured 1,4-dioxane concentration; i.e., 1,4-dioxane is being degraded. Thus no increase in optical density will be seen in the absence of 1,2-dioxane and no decrease in 1,2-dioxane will seen when the organism is not present. 1,4-Dioxane ("DX") removal therefore depends on the presence of CB1190. This can be seen from the following:

| | CB1190 | | Abiotic Control | | No Dioxane |
|---|---|---|---|---|---|
| | DX | | | | |
| Hours | (ppm) | $OD_{660}$ | DX (ppm) | $OD_{660}$ | Control $OD_{660}$ |
| 0 | 536 | 0.070 | 425 | 0.000 | 0.080 |
| 5 | 523 | 0.075 | 431 | 0.000 | 0.059 |
| 23 | 488 | 0.079 | 425 | 0.000 | 0.072 |
| 29 | 442 | 0.107 | 410 | 0.000 | 0.070 |
| 53 | 338 | 0.174 | 412 | 0.000 | 0.064 |
| 75 | 91 | 0.288 | 429 | 0.000 | 0.068 |

In practice, the dioxane degrading organism can be utilized in a bioreactor. A variety of reactor configurations including packed bed reactors, continuous stirred tank reactors, rotating biological contactors, sequencing batch reactors, and fluidized bed reactors, can be utilized. Additionally, the dioxane degrading organism can be used in situ at dioxane contaminated sites.

Reactor operation usually requires supplementation with a basal salts nutrient medium. Media such as that described infra can be used, typically in a concentration of 0.1× to 1×, although other nutrients can be substituted provided that the nutritional requirements (such as nitrogen, phosphorous, magnesium, etc.) of bacteria are met.

The pH in the reactor should be controlled so as to lie within the range of from about 5 to about 8, normally through adjustment of the feed stream with a base such as sodium hydroxide or an acid such as sulfuric acid, as the case may be. Dioxane degradation per se typically does not result in a major change in the pH of culture but degradation of other pollutants in the pollutant stream or of 1,4-dioxane in high concentrations can lead to a change in pH in the reactor.

The temperature of the feed stream and/or of the reactor can be adjusted in order to optimize the effectiveness of the organism. If, for example, the temperature of the influent is excessively low, it can be heated. If the influent is not heated, the rate will be lower and the reactor will be less efficient. A reactor then will need to be larger in order to compensate for the decreased efficiency.

The 1,4-dioxane degrading microorganism can be used either as a pure culture or in a mixed culture. Hence while isolation of the pure culture permits identification of the operative species, it is not necessary to utilize the culture in its pure form. Consortia containing the operative species also can be used. For example, the consortium CB1184 degraded the 1,4-dioxane in groundwater contaminated with other organics from a level of 13 ppm to <1 ppm within 24 hours. 1,4-Dioxane at a level of 23 ppm in a process stream similarly was degraded by the same consortium to <1 ppm. The consortium designated CB1185 reduced 1,4-dioxane in a groundwater sample from 18.7 ppm to <10 ppb within 24 hours. In fact even starting with the biologically pure culture, the presence of other organisms (generally originating from the nonsterile influent) can be detected after the reactor is placed in use.

The examples which follow will serve to further typify the invention but should not be construed as a limitation on the scope of the invention which is defined only by the appended claims.

METHODS AND MATERIALS

The following stock solutions are used herein. The precise compositions are not critical but are standardized to eliminate variables.

| Basal Salts Medium (BSM): | |
| --- | --- |
| Water | 800.0 mL |
| Buffer Stock (10X) | 100.0 mL |
| Trace Metals Stock (10X) | 100.0 mL |
| Buffer Stock (10X) | |
| $K_2HPO_4$ | 32.4 g |
| $NaH_2PO_4.H_2O$ | 10.0 g |
| $NH_4Cl$ | 20.0 g |
| Water | 1000.0 mL |
| Trace Metals Stock (10X) | |
| Nitrilotriacetic acid (disodium salt) | 1.23 g |
| $MgSO_4.7H_2O$ | 2.00 g |
| $FeSO_4.7H_2O$ | 0.12 g |
| $MnSO_4.H_2O$ | 0.03 g |
| $ZnSO_4.7H_2O$ | 0.03 g |
| $CoCl_2.6H_2O$ | 0.01 g |
| Water | 1000.0 mL |
| Ammonium Mineral Salts Medium (AMS): | |
| $(NH_4)_2SO_4$ | 0.66 g/l |
| $MgSO_4.7H_2O$ | 1.0 g/l |
| $CaCl_2.2H_2O$ | 0.015 g/l |
| Trace Elements | 1.0 mL/l |
| Stock A | 1.0 mL/l |
| 1 M Phosphate (added after autoclaving) | 20.0 mL/l |
| Trace Elements: | |
| $FeSO_4.7H_2O$ | 500 mg/l |
| $ZnSO_4.7H_2O$ | 400 mg/l |
| $MnSO_4.4H_2O$ | 20 mg/l |
| $H_3BO_3$ | 15 mg/l |
| $NiCl_2.6H_2O$ | 10 mg/l |
| EDTA | 250 mg/l |
| $CoCl_2.6H_2O$ | 50 mg/l |
| $CuCl_2.2H_2O$ | 5 mg/l |
| Stock A: | |
| Fe—Na EDTA | 5 g/l |
| $NaMoO_4.2H_2O$ | 2 g/l |
| 1 M Phosphate: | |
| $K_2HPO_4$ | 113 g/l |
| $KH_2PO_4$ | 47 g/l |

AMS plates are made by adding 1.5% Noble Agar (Difco) to the medium.

EXAMPLE 1

An initial enrichment culture is inoculated with a 1,4-dioxane-containing industrial sludge obtained from Darlington, SC. The sludge is incubated aerobically in BSM plus 0.1% w/v yeast extract in the presence of 100–300 ppm of tetrahydrofuran (THF). Once degradation of THF is established, the enrichments are supplied with both THF and 100–500 ppm of 1,4-dioxane. Activity with respect to both THF and 1,4-dioxane can be seen on several enrichments; dioxane degradation does not appear to be observed unless THF is supplied. Transfer cultures of these enrichments degrade THF and 1,4-dioxane to <1 ppm within 78 hours in sealed reactors.

The transfer cultures from the initial enrichments are combined and placed in an aerated 10L fermenter containing BSM and 0.1% w/v yeast extract. This culture is supplied with THF and dioxane. After the THF is depleted, only dioxane is supplied and degradation is allowed to continue in the absence of THF. Eventually 1000 ppm of 1,4-dioxane can be supplied to the culture daily. This culture, designated CB1184, consists of a mixed population which includes irregularly branched, filamentous organisms with clumps or mats of organisms forming within these filaments. The ability of CB1184 to degrade 1,4-dioxane, even in the presence of increasing 1,4-dioxane concentrations, is seen from the following:

| Time | Concentration of 1,4-Dioxane (ppm) | | | | |
| --- | --- | --- | --- | --- | --- |
| (Hours) | Live cultures | | | | Sterile |
| 0 | 128 | 218 | 510 | 1023 | 989 |
| 2 | 122 | 202 | 497 | 1002 | 985 |
| 4 | 111 | 186 | 428 | 868 | 997 |
| 6 | 88 | 149 | 353 | 803 | 989 |
| 8 | 72 | 121 | 269 | 623 | 992 |
| 10 | 48 | 83 | 228 | 401 | 987 |
| 12 | 34 | 35 | 164 | 222 | 989 |

EXAMPLE 2

Continued transfer and enrichment of CB1184 in the presence of 100 ppm cycloheximide, high levels of 1,4-dioxane (5000–10,000 ppm), and no yeast extract produced a new enriched culture which also contains filamentous, irregularly branched procaryotic organisms. This culture was given the designation CB1185.

CB1185 can degrade ~100 ppm of 1,4-dioxane to <20 ppb in less than 4 hours as can be seen from the following:

| Time | Concentration (ppm) | | |
| --- | --- | --- | --- |
| (Hours) | 1X cells | 2X cells | Sterile |
| 0 | 101 | 111 | 108 |
| 1 | 67 | 47 | 113 |
| 2 | 37 | 16 | 109 |
| 3 | 17 | 0.08 | 104 |
| 4 | 0.12 | 0.02 | 110 |
| 5 | 0.02 | 0.02 | 107 |
| 6 | 0.02 | 0.02 | 109 |
| 7 | 0.02 | 0.02 | 108 |

As seen from the above, a doubling of the catalyst concentration increases the volumetric rate of degradation.

Low concentrations of 1,4-dioxane (<2 ppm) also are rapidly degraded to <10 ppb. When catalyst concentration is held constant and the initial 1,4-dioxane concentration is increased, the specific rate of 1,4-dioxane degradation increases.

| (Hours) | Concentration (ppb) | | | |
| --- | --- | --- | --- | --- |
| 0 | 1300 | 760 | 440 | 200 |
| 1 | 493 | 525 | 206 | 82 |
| 2 | <10 | <10 | <10 | <10 |
| 4 | <10 | <10 | <10 | <10 |
| 6 | <10 | <10 | <10 | <10 |

In general, when 1,4-dioxane concentrations are held near 300 ppm, the specific activities (µg dioxane degraded per min per mg biomass protein) range from 0.2 to 1.2.

EXAMPLE 3

CB1185 culture was streaked onto plates containing AMS and 2000 ppm 1,4-dioxane. Resulting colonies were rough and irregular in shape, dry and white on the top, and pale orange underneath. Microscopic observation (1000×) indicated that while the colonies were not pure, they contained irregularly branching filamentous organisms as well as two or three types of typical bacterial rods. An isolated colony was transferred to a fresh AMS 1,4-dioxane plate which was incubated at 30° C. for about 3 weeks.

One isolated colony, which was still not a pure culture, was streaked onto an AMS plate containing 2000 ppm 1,4-dioxane. The culture was incubated at 30° C. for 2 weeks. Observation (1000× magnification) indicated a pure culture of irregularly branching filaments with no small rods. A single colony was inoculated into 50 mL of AMS containing 331 ppm of 1,4-dioxane and placed on a shaker at room temperature. 1,4-Dioxane concentration was monitored by GC periodically. To insure that the culture was pure, an isolated white colony was streaked onto AMS plus 2000 ppm 1,4-dioxane, AMS plus 10 mM succinate, AMS with no carbon source, Luria agar, and Difco Actinomycete Isolation Agar. The plates were incubated at 30° C. for about one week. A single colony type grew on all plates except Luria agar, where only background growth was seen. A suspension of this growth was observed at 1000× magnification, and only filamentous or branching rods were seen, indicating the culture was likely to be pure. A single white colony from AMS plus 2000 ppm 1,4-dioxane was streaked onto AMS plus 1000 ppm 1,4-dioxane (with and without streptomycin at 100 µg/mL), AMS plus 10 mM succinate, AMS with no carbon source, and Actinomycete Isolation Agar. Plates were incubated at 30° C. for about 1 week. Colonies grew on all media types except in the presence of streptomycin, and appeared similar to white colonies obtained from Example 4 under the dissecting microscope. The culture was designated CB1190.

EXAMPLE 4

Orange, filamentous clumps from CB1185 were plated onto soft agar (0.3% Noble agar) AMS plates containing 1000 ppm 1,4-dioxane and incubated at 30° C. for one week. Plates then were left at room temperature for approximately one month. An isolated orange colony was removed from the plate and grown overnight in 5 mL LB on a shaker (250 rpm) at 30° C. The culture was centrifuged for 5 min. at 14,000 rpm, room temperature, then resuspended in an equal volume of AMS. 100 µL of dilutions from $10^0$–$10^{-10}$ were plated onto AMS containing 2000 ppm 1,4-dioxane (1.5% agar) and Actinomycete Isolation Agar. Plates were incubated at 30° C. for approximately one week and then placed at room temperature for a week. Among several other colony types, fifty to sixty dry white colonies were seen on the $10^0$ plate, and three of the same type were seen on the $10^{-1}$ plate, both for the AMS/1,4-dioxane and Actinomycete agar plates. Single colonies were streaked onto plates of AMS plus 1000 ppm 1,4-dioxane, AMS plus 10 mM succinate, AMS with no carbon source, and Actinomycete Isolation Agar. The plates were incubated at 30° C. for 6 days. Growth of the dry white colonies was observed on all plates within one week, including the no carbon source plate. Colonies were picked and restreaked from these plates onto AMS plus 1000 ppm 1,4-dioxane ±-streptomycin (100 µg/mL), AMS plus 10 mM succinate, AMS with no carbon source, and Actinomycete Isolation Agar. Plates were incubated at 30° C. for one week. The dry white colony type grew on all media types except medium containing streptomycin.

Observation with the dissecting microscope revealed single colonies with feathery edges. Some colonies appeared to have a budding, liquid bubble at the center of the colony. Under higher magnification (1000×), large, stationary branching rods and small motile rods were seen. An isolated colony from AMS plus 1000 ppm 1,4-dioxane and one from Actinomycete Isolation Agar were streaked onto AMS plus 1000 ppm 1,4-dioxane, AMS with no carbon source, and Actinomycete Isolation Agar. Again, no growth was seen on streptomycin plates, but isolated white colonies grew on the other types of media. Under higher magnification (1000×), stationary, branching, thick rods with some bulbous areas were seen, this time in the absence of any other organism. Morphology was similar to that observed in Example 3.

EXAMPLE 5

The specific activity of CB1190 (sealed bottle assays) with an initial 1,4-dioxane concentration of 500 ppm was 0.33 µg/min-mg protein. CB1185 had a specific activity of 0.24 µg/min-mg protein in similar assays performed at the same time.

Mineralization of 1,4-dioxane was tested in sealed 160 mL serum bottles with CB1185 and CB1190. The cultures were prepared in BSM, washed, resuspended, and incubated with or without 350 ppm 1,4-dioxane for 18 hours. Carbon dioxide in the liquid and headspace was measured in these cultures. The production of endogenous $CO_2$ was determined in the cultures that did not receive 1,4-dioxane. The averages of three replicate samples are as follows, standard deviations being shown in parentheses:

|  | 1,4-Dioxane consumed (mg C) | Total $CO_2$ produced (mg C) | Endogenous $CO_2$ (mg C) | Total minus endogenous | % dioxane converted to $CO_2$ |
| --- | --- | --- | --- | --- | --- |
| CB1190 | 4.15 (0.00) | 3.87 (0.07) | 1.40 (0.00) | 2.47 (0.07) | 59.5 (1.8) |
| CB1185 | 5.06 (0.96) | 6.31 (1.8) | 3.45 (0.00) | 2.86 (1.8) | 53.5 (26.1) |

As shown by the above, over 50% of the 1,4-dioxane carbon content is released as $CO_2$ by both cultures.

EXAMPLE 6

A 2-liter glass reactor vessel was filled with CB1184 culture and operated as a continuous stirred tank reactor (CSTR). BSM (1×) containing 1,4-dioxane was pumped to the reactor. The reactor was stirred with a magnetic stir bar and the liquid volume was maintained at 1100 mL by an effluent pump. The effluent from the reactor entered the clarifier, where the bacteria were settled to the bottom by gravity, and the clarified effluent exited through the drain. The bacteria which collected in the clarifier were manually added back to the reactor on a daily basis.

The flow rate to the reactor was set at 0.3 mL/min, the concentration of 1,4-dioxane in the feed was 100 ppm, and the aeration rate was 200 mL/min of prehumidified air. Under these conditions, the effluent concentration of 1,4-dioxane was measured at 420 ppb. The protein concentration in the reactor was 700 mg/l. The volumetric rate of 1,4-dioxane degradation was calculated to be 0.0018 g/l-hr. The residence time in the reactor was 2.5 days.

In a second run, the flow was set at 0.42 mL/min, the feed 1,4-dioxane concentration was 1200 ppm, and the aeration rate was 1200 mL/min of humidified air. The effluent 1,4-dioxane concentration was 270 ppm. The volumetric rate was calculated to be 0,024 g/l-hr and the residence time was 1.8 days.

EXAMPLE 7

A rotating biological contactor (RBC), or rotating disk biological contactor was constructed with disks 4.5 inches in diameter and 0.25 inches in thickness. The disks were mounted so that approximately 40% of the diameter was submerged in the reactor liquid and the shaft was rotated at 11 rpm. This rotation rate translated to a perimeter velocity of 4 meters/min. The reactor liquid inlet and liquid outlet were mounted at opposite corners of the reactor in order to minimize channeling of the liquid flow. A culture of CB1184 was added to the reactor and a flow of different concentrations of 1,4-dioxane in 1× BSM was run through the reactor at different flow rates for a period of weeks in order to start the reactor. The culture attached to the disks over this time period. The concentration of 1,4-dioxane in the feed then was set at 91 ppm and the flow rate was set at 0.29 mL/min. The effluent concentration decreased to 1 ppm. The residence time in this reactor was 2.3 days and the volumetric degradation rate was calculated to be 0.0018 g/l-hr.

In a second experiment, the feed concentration of 1,4-dioxane was 5000 ppm, the flow rate was 0.29 mL/min., and the effluent concentration was 1800 ppm. The volumetric degradation rate was calculated to be 0,054 g/l-hr.

EXAMPLE 8

Packed bed reactors in the form of glass columns, 1 inch in diameter and 12 inches in height, were erected with (i) open-cell polyurethane foam cut into cubes approximately 5 mm on a side (characteristics: 25% deflection at 0.42 psi, density =2.8 lb/ft$^3$ and tensile strength =9 psi), (ii) granular activated carbon (12×40 mesh), (iii) 30–100 mesh silica sand, (iv) 40–60 mesh glass beads, and (v) a mixture of delrin, nylon, acrylic, teflon, and polypropylene spheres (0.25 inch diameter). The superficial reactor volume was 150 mL.

Culture CB1184 was added to these reactors by recycling a given volume of culture through each column so that the final concentration of protein in the reactor was approximately 3000 mg protein/liter reactor volume. Air and liquid were introduced into the top of the reactor columns and flowed concurrent and downward through the reactors. 1,4-Dioxane degradation was observed immediately in all but the granular activated carbon reactor.

All reactors showed high percent removals of 1,4-dioxane. In the GAC, sand, glass and foam reactors the feed concentration was 100 ppm, the liquid flow rate was 0.28 mL/min and the air flow rate was 100–200 mL/min. The effluent concentration was <40 ppb for all of these reactors. The volumetric rate of 1,4-dioxane degradation was calculated to be 0.012 g/l-hr based on the superficial reactor volume. The superficial hydraulic residence time was 9 hours.

In a further experiment, a glass column was filled with 6×9 mesh spherical silica sand and loaded with culture CB1185. 1,4-Dioxane at concentrations of 2 ppm and 100 ppm, was fed to the reactor at 0.3 mL/min. The 1,4-dioxane concentration in the effluent was <50 ppb under both conditions.

EXAMPLE 9

A large scale packed bed reactor was used to treat the actual ground water contaminated with 1,4-dioxane, as well as other compounds including biphenyl, biphenyl ether, ethylene glycol, chlorobenzene, acetone, chloroform, 1,1-dichloroethane, 1,1-dichloroethene, 1,2-dichloroethene, methylene chloride, 1,1,1-trichloroethane, and toluene. The reactor was 6 inches in diameter with a bed height of 7 feet and a reactor volume of approximately 40 liters. The reactor was packed with 6×9 mesh spherical silica sand and loaded with 30 gal of CB1185 culture. The 30 gal CB1185 containing 840 ppm 1,4-dioxane was recycled through the reactor for 24 hr. at 0.23 L/min. Air flow was 7.0 L/min. The protein concentration in the reactor was estimated to be roughly 5–6 g/l.

A stream of 1,4-dioxane 1000 ppm in 1.0× BSM first was recycled through the reactor for 6.5 days and then continuous flow of influent without recycle was initiated. The concentration of 1,4-dioxane was 250 ppm and the liquid flow was 0.05 l/min. The air flow was 1.0 l/min. All flows were concurrent and downward. Under these conditions, the effluent concentration ranged from <1 ppm to 40 ppm depending on the temperature. For example, when the effluent temperature was low, about 15° C., the influent and effluent 1,4-dioxane concentrations were 255 ppm and 39.7 ppm, respectively, and the volumetric degradation rate was calculated to be 0.016 g/l-hr. When the temperature was 27.4° C., the influent and effluent concentrations were 250 ppm and <1 ppm respectively and the rate was calculated to be 0.019 g/l-hr. At ambient temperatures (approximately 23°–27°C.) the maximum flow rate allowable while maintaining <1 ppm 1,4-dioxane in the effluent was determined over short periods of time. The air:liquid flow ratio (vol:vol) was maintained at approximately 10:1. The maximum liquid flow rate was 0.55 l/min for an influent concentration of 11–13 ppm. The volumetric rate of 1,4-dioxane degradation was calculated to be 0.0099 g/l-hr. The maximum liquid rate was 1.3 l/min for an influent concentration of 3–4 ppm. The volumetric rate of 1,4-dioxane degradation was calculated to be 0.0068 g/l-hr.

Actual ground water then was run through the reactor. The ground water from well EW-11 was expected to contain 4745 ppb of 1,4-dioxane and a COD of 14 ppm. The actual concentration of 1,4-dioxane was 5026 ppb (SE=67 ppb). At a liquid flow rate of 0.8 l/min, the effluent concentration was 40–80 ppb. The air flow rate was 2.0 l/min. The volumetric rate of 1,4-dioxane degradation was calculated to be 0,006 g/l-hr. The effluent temperature was 19°–22° C.

EXAMPLE 10

A glass column 1 inch in diameter and 12 inches in height was filled with 150 mL of 6 by 9 mesh silica sand. The sand was washed with water and then 1 liter of strain CB1190 was circulated through the sand under total recycle for 12 hours. The flow rate of liquid was 10 mL/min and the flow rate of air was 150 mL/min. After this time, the concentration of protein on the sand was estimated to be 500 mg protein/liter sand. The air flow rate was kept constant at 150 mL/min and a 0.3 mL/min of 100 ppm 1,4-dioxane in 1×BSM plus 1 mM $NaHCO_3$ was initiated. The effluent concentration was <1 ppm after 1, 2 and 3 days of operation.

EXAMPLE 11

A sequencing batch reactor (SBR) was constructed by fitting a 2L glass reactor vessel with an influent pump, effluent pump, humidified aeration system, magnetic stirring, sample pump, and electronic relays to automatically control the reactor. The working volume of the reactor was 1200 mL. The reactor was filled with CB1190 culture and operated on the following cycle with periodic sampling as follows:

1. Settle: Stirring and aeration were terminated for 50 minutes, allowing the biomass to settle to the bottom of the reactor.
2. Drain: The effluent pump was turned on for 3 minutes and a preset percentage of the clarified liquid was drained.
3. Idle: All equipment turned off for 4 minutes (or sufficient so that periods 1–4 totalled 60 minutes).
4. Fill: The influent pump was turned on for 3 minutes, and sufficient feed composed of nutrients (1× BSM) and 1,4-dioxane was added to bring the total volume back up to 1200 ml.
5. React: Aeration and stirring were instituted for a time sufficient to degrade the 1,4-dioxane in the reactor.

After period 5, the automatic controller loops back to period 1. Total cycle time was equal to 1 hour plus the time selected for period 5.

The conditions used in one experiment were 24 hour cycle time, 100 ppm 1,4-dioxane in the feed, and 425 mL fill/drain volume (35% of working volume). Under these conditions, the effluent concentration was <1 ppm and the protein concentration in the reactor was 400 mg/l. The volumetric rate was 0.0018 g/l-hr.

In another experiment, a similar reactor was set up with culture CB1185 attached to mammalian cell microcarriers (Cultisphere-S, Hyclone Laboratories, Logan, Utah) in order to increase biomass retention in the reactor. One hundred milliliters of microcarriers were used in the 1200 mL working volume reactor. The cycle time was 12 hours, the fill/drain volume was 150 mL (12.5% of working volume), and the feed concentration of 1,4-dioxane was 1200 ppm. The effluent concentration of 1,4-dioxane was <1 ppm and the protein concentration was 1200 ppm. The volumetric rate of 1,4-dioxane degradation was 0.25 g/l-hr.

EXAMPLE 12

A fluidized bed reactor (FBR) constructed from a glass column 2 inches in diameter and 4 feet in height was filled with granular activated carbon (12×40 mesh). Culture CB1185 was added to the reactor by recycling a given volume of culture through the column so that a final concentration of protein in the reactor was approximately 480 mg protein/liter of reactor. The reactor was initially operated as a packed bed with concurrent and downward air and liquid flow. Air and liquid was introduced into the top of the column and flowed concurrent and downward through the reactor. 1,4-Dioxane was supplied at 1000 ppm.

After 2 weeks of operation in this mode, the liquid flow was reversed and air was supplied through a recycle line so that the reactor was operating as a non-fluidized packed upflow reactor (reactor volume =2.2 liters). The 1,4-dioxane feed was supplied at 1000, 500, and then 100 ppm. The liquid flow was 300 ml/min and the recycle to flow ratio was 40:1. After 3 weeks the feed remained at 100 ppm and the effluent was below 1 ppm.

The column was then fluidized by increasing the recycle flow. The feed concentration was set at approximately 1500–2000 ppm and the base of the column has received from 2 to 160 ppm 1,4-dioxane. The feed flow has been run from 1.5 to 6.25 ml/min and the recycle flow has been set at 500 ml/min. Degradation of 1,4-dioxane across the column has been approximately 5–10 ppm. When influent levels of 1,4-dioxane are maintained below 10 ppm then <1 ppm 1,4-dioxane has been observed in the effluent. 1.71 g/l of 1,4-dioxane was consumed (feed concentration minus effluent concentration) with a feed flow of 0.15 l/hr. and a reactor volume of 2.2 liters (expanded bed volume of 1.785 liters). This calculates to a productivity of 0.117 g/l-hr based on the reactor volume.

EXAMPLE 13

CB1190 was incubated at 30° C. in sealed bottles or flasks containing AMS medium containing the ether. Growth of CB1190 was determined by a significant increase in optical density at 660 nm within 1 week (at least two doublings). Under these conditions growth was observed with 500 of either ppm 1,4-dioxane, 1,3-dioxane, tetrahydrofuran, tetrahydropyran, diethyl ether, and butyl methyl ether, separately. CB1190 doubled in density when grown with 300 ppm 2-methyl-1,3-dioxolane. GC experiments indicated complete removal of 2-methyl-1,3-dioxolane by CB1190. Growth was also observed upon serial transfer of CB1190 to fresh medium containing the same ether growth substrates.

What is claimed is:

1. A process for the degradation of ethers which comprises bringing an ether-containing liquid influent into intimate contact, with a culture comprising an actinomycete, genus Amycolata, having all identifying characteristics of ATCC 55486, or a mutant thereof which retains the characterizing microbiological property of being capable of utilizing dioxane as a sole carbon growth source, in the presence of oxygen, and under growth or resting conditions permitting said actinomycete or said mutant thereof to utilize the ether as a carbon source, thereby degrading said ether.

2. The process according to claim 1 in which the process is conducted at a pH maintained at from about 5 to about 8.

3. The process according to claim 1 in which the process is conducted at temperatures of from about 10° C. to about 42° C.

4. The process according to claim 1 in which said ether-containing influent is brought into contact with said culture in a fluidized bed reactor.

5. The process according to claim 1 in which said ether-containing influent is brought into contact with said culture in a packed bed reactor.

6. The process according to claim 1 in which said ether-containing influent is brought into contact with said culture in a sequencing batch reactor.

7. The process according to claim 1 in which said ether-containing influent is brought into contact with said culture in a rotating biological contactor.

8. The process according to claim 1 in which said ether-containing influent is brought into contact with said culture in a continuous stirred tank reactor.

9. A process for the degradation of dioxanes which comprises bringing a dioxane-containing liquid influent into intimate contact, in the presence of oxygen, at a temperature of from about 10° C. to about 42° C., and at a pH of from about 5 to about 8, with a culture comprising an actinomycete, genus Amycolata, ATCC 55486 or a mutant thereof which retains the characterizing microbiological property of the parent microorganism of being capable of utilizing dioxane as a sole carbon source, and under suitable conditions permitting said actinomycete or said mutant thereof to utilize the dioxane as a carbon source, thereby degrading said dioxane.

10. A biologically pure culture of Amycolata ATCC 55486, or a mutant thereof possessing the capability of the parent microorganism of using dioxane as a sole carbon source.

* * * * *